United States Patent [19]

Drent et al.

[11] Patent Number: 5,364,970
[45] Date of Patent: Nov. 15, 1994

[54] PROCESS FOR THE HYDROFORMYLATION OF UNSATURATED CARBONYL COMPOUNDS

[75] Inventors: Eit Drent; Eric Kragtwijk, both of Amsterdam, Netherlands

[73] Assignee: Shell Oil Company, Houston, Tex.

[21] Appl. No.: 186,749

[22] Filed: Jan. 25, 1994

[30] Foreign Application Priority Data

Jan. 25, 1993 [NL] Netherlands .................. 93200185

[51] Int. Cl.$^5$ .............................................. C07C 45/10
[52] U.S. Cl. .................................. 568/454; 568/451; 568/882; 562/519; 560/174
[58] Field of Search ............. 560/174, 175; 568/451, 568/454, 455, 882; 562/519

[56] References Cited

U.S. PATENT DOCUMENTS

| | | | |
|---|---|---|---|
| 4,001,336 | 1/1977 | Hoffman | 260/601 R |
| 4,201,728 | 5/1980 | Hughes | 568/454 |
| 4,344,896 | 8/1982 | Kurkov | 260/465.1 |
| 4,849,543 | 7/1989 | Lin | 560/177 |
| 5,264,616 | 11/1993 | Roeder et al. | 560/175 |
| 5,268,514 | 12/1993 | Bahrmann et al. | 568/882 |
| 5,281,751 | 1/1994 | Schreck | 562/519 |

FOREIGN PATENT DOCUMENTS

| | | |
|---|---|---|
| 0073398A1 | 3/1983 | European Pat. Off. . |
| 0073961A1 | 3/1983 | European Pat. Off. . |
| 0375573A1 | 6/1990 | European Pat. Off. . |
| 1040434A | 2/1989 | Japan . |
| 2014138A | 8/1979 | United Kingdom . |
| 2100260A | 12/1982 | United Kingdom . |

OTHER PUBLICATIONS

Tanaka et al., Diphosphine-Rhodium Complex-Catalyzed Hydroformylation of $\alpha,\beta$-Unsaturated Esters, *Bulletin of the Chemical Society of Japan*, vol. 50 (9), 2351–2357 (1977).

Pittman Jr., et al., Hydroformylation of Methyl Methacrylate Catalyzed by Homogeneous and Polymer-Attached Rhodium Complexes, *J. Org. Chem.*, 1980, 45, 684–689.

*Primary Examiner*—Arthur C. Prescott

[57] ABSTRACT

A process for the hydroformylation of $\alpha$-substituted, $\alpha$-$\beta$-unsaturated carbonyl compounds in the presence of a catalyst system based on
  a) a source of rhodium cations and
  b) a source of ligands of the formula $MR_1R_2R_3$ wherein M represents a phosphorus, arsenic or antimony atom and $R_1$, $R_2$, and $R_3$ independently represent substituted or non-substituted hydrocarbyl groups, together containing not more than 24 carbon atoms. At least one of $R_1$, $R_2$, and $R_3$ is linked to M via an aliphatic carbon atom. The process is selective for the generation of alpha reaction products.

20 Claims, No Drawings

PROCESS FOR THE HYDROFORMYLATION OF UNSATURATED CARBONYL COMPOUNDS

BACKGROUND OF THE INVENTION

This invention relates to the hydroformylation of unsaturated compounds.

The hydroformylation of ethylenically unsaturated compounds is a well known process of considerable industrial importance. Generally, hydroformylation reaction involve the reaction of carbon monoxide and hydrogen in the presence of a catalyst with the double bond of a compound $C_1 = C_2$ to form a compound containing one carbon atom more than the starting material. The product usually contains an aldehyde group but may form other products such as alcohols, or a mixture of aldehydes and alcohols depending upon the catalyst and reaction conditions such as the hydrogen/carbon monoxide ratio.

The aldehyde groups or alcohol groups ($-CH_2OH$), may be linked to either $C_1$ or to $C_2$. If the groups bound to the free valencies of $C_1$ are the same as the groups bound to the free valencies of $C_2$ a single hydroformylated product will generally be formed. However, if different groups are attached to $C_1$ and $C_2$, the reaction product can be a mixture of different hydroformylated products, i.e. a mixture of different aldehydes and/or different alcohols. For example, starting from methylacrylate, hydroformylation might be expected to yield a mixture of methyl α-formylpropionate and methyl α-formylpropionate.

Electronic and/or stearic factors of the reactants, catalysts, and associated ligands can have a pronounced effect on the distribution of hydroformylation products. That is, some reaction products are generally impeded or prevented from forming in favor of others. Thus, lower notwithstanding that different groups are attached to the free valencies of $C_1$ and $C_2$, a single hydroformylated product generally predominates. In the case of the hydroformylation of methacrylic acid, for example, β-formylmethacrylic acid, rather than α-formylmethacrylic acid, is generally the predominant hydroformylated product.

In many instances, it would be desirable if the α-formyl product could be selectively obtained. The formation of α-formylcarbonyl compounds is particularly interesting given their utility as intermediates for the production of specialty chemicals such as malonates of lactones and for pharmaceutical compounds. For example, U.S. Pat. No. 4,001,336 to Hoffman discloses the use of α-formylpropionic acid methyl ester in the production of 2,6,10-trimethyl-dodecan-1-al, an artificial flavoring.

Accordingly, attempts have been made to develop suitable catalyst systems and to establish the reaction conditions that favor the formation of the α-formyl products. Unfortunately, even where desired hydroformylation product have been formed with adequate selectivity, the reaction rates have been disappointingly low. Raising the reaction temperature has been considered as a means for increasing the rate but the stability of the catalyst is adversely affected at temperatures needed to meaningfully increase the reaction rate. Moreover, raising the reaction temperature proliferates undesired reactions such as double bond hydrogenation and polymerization at the expense of the selectivity to the desired hydroformylated compound.

M. Tanaka et al. in Bull. Chem. Soc. Japan, vol 50 (9), pp. 2351-2357 (1977) have published results of the hydroformylation of α-β-unsaturated esters. They indicated the preferred conditions and catalyst systems for the selective formation of some α-formylated products. The Authors reported attaining selectivities of 95% and greater of the ethyl-α-formylpropionate product from the hydroformylation of ethylacrylate results in selective formation. However, this figure only denotes the proportion of α-formylpropionate related to the total amount of hydroformylated products. Thus, it ignores the formation of considerable amounts of hydrogenated product (ethylpropionate). Inclusion of these and other hydroformulated products would certainly bring the selectivity figures well below the reported 95% selectivity. Moreover, the highest selectivity obtained in hydroformylating an α-substituted, α-β-unsaturated ester using a catalyst containing rhodium and 1,3-bis(diphenylphosphino) propane as ligand, was 81.4%. This too ignored the formation of saturated byproduct.

While the nature of the rhodium based catalysts themselves were addressed, perhaps the most important proposition preferred in the article by Tanaka et. al. was the relationship between ligand configuration and catalytic activity. The authors took the position that there is an optimum carbon chain length of about $C_2$ to $C_4$ between ligand phosphine moieties for increasing alpha selectivity of hydroformylation products. Interestingly, the authors selected only diphosphines substituted with bulky aryl or cyclic substituents. 1,2-bis(diphenylphosphino)ethane appeared to be most preferred.

The prominence of phosphine derivatives substituted with numerous bulky aryl or cyclic substituents has continued to this day. For example, EP 0375573 to Devon et al, selected ligands such as α,α-bis(diphenylphosphino)-o-xylene for use in conjunction with a rhodium based catalyst in the hydroformylation of lower olefins. U.S. Pat. No. 4,201,728 to Hughes employs ligands such as trans 1,2-bis(diphenylphosphinomethyl) cyclobutane to increase alpha selectivity of aldehyde hydroformylation products. Japanese Patent JP 1040-434-A to Kuraray disclosed the use of a tris (substituted phenyl) phosphite with a rhodium compound for the hydroformylation of vinyl compounds.

Throughout the prior art, alpha selectivity of the products of olefinic hydroformylation is wildly divergent when such ligands are present. None of the art cites alpha selectivities consistently greater than 75% (based on the total quantity of reaction products) across a range of proposed ligands and reaction conditions for the production of a given olefinic hydroformylation product. Indeed, it is more often the case that alpha selectivities below 50% (based on the total quantity of reaction products) are found among a class of ligands claimed in the production of a given olefinic hydroformylation product.

Hence, the need to define a hydroformylation process which consistently attains highly selective α-formylated products has not abated.

SUMMARY OF THE INVENTION

It is an object of this invention to provide a hydroformylation process that selectively produces α-formylated products.

It is a further object of this invention to provide a hydroformylation process with improved α-formylation selectivity without substantially diminishing reaction rates.

It is a yet further object of this invention to define a catalyst system which consistently produces improved α-formylation products of unsaturated carbonyl compounds.

It is a yet further object of this invention to define a class of ligands which optimize the α-selectivity of catalysts used in the hydroformylation of unsaturated carbonyl compounds.

In accordance with this invention a hydroformylation process is provided comprising reacting α-substituted, α-β-unsaturated carbonyl compounds with carbon monoxide and hydrogen in the presence of a catalyst system comprising:

a) a source of rhodium cations; and
b) a source of ligands of the formula $MR_1R_2R_3$ wherein M is a member the group consisting of phosphorus, arsenic and antimony; $R_1$, $R_2$ and $R_3$ are independently selected from the group consisting of hydrocarbyl groups and substituted hydrocarbyl groups. The hydrocarbyl and substituted hydrocarbyl groups together do not contain more than 24 carbon atoms. Further, at least one of $R_1$, $R_2$ and $R_3$ is linked to M by an aliphatic carbon atom.

DETAILED DESCRIPTION OF THE INVENTION

Surprisingly, it has now been found that highly selective β-formylated products can be consistently obtained from the hydroformylation of olefinic reactants by using a rhodium-based catalyst system which employs a selected class of stabilizing ligands.

Without being bound to theory, it is believed that the coordination between the rhodium ion and the ligand is of great importance. Both stearic and electronic factors, determined by the structure of the ligand, will affect the nature of this metal-ligand coordination. It has been observed that with monodentate ligands comprising three aryl groups linked to the atom M and with ligands containing more than 24 carbon atoms, the coordination with the rhodium ion is non-optimal as regards the alpha selectivity of the hydroformylation reaction. The structure of ligands which are considered more suitable in this respect is thus indicated herein.

The ligands are of a general class depicted as $MR_1R_2R_3$. M may be either phosphorus, arsenic or antimony. Phosphorous is preferred. $R_1$, $R_2$ and $R_3$ may each be a substituted or unsubstituted hydrocarbyl group. However, $R_1$, $R_2$ and $R_3$ do not contain more than 24 carbon atoms all together. Further, at least one of $R_1$, $R_2$ and $R_3$ is linked to M by an aliphatic carbon atom.

In another embodiment, the ligands are of a general class depicted as $R_1R_2MR_4MR_5R_6$. In this case, M, $R_1$, $R_2$, and $R_3$ have the same meaning as set forth above. $R_4$ is a bivalent organic group, $R_5$ and $R_6$ are substituted and unsubstituted hydrocarbyl groups.

If each of $R_1$, $R_2$ and $R_3$ represents a nonsubstituted hydrocarbyl group, or a hydrocarbyl group substituted with one or more substituents that do not form a complexing linkage with rhodium, the ligand is a monodentate ligand. If the catalyst system of the invention is based on a monodentate ligand, each of $R_1$, $R_2$, and $R_3$ preferably represents a substituted or non-substituted alkyl group. Examples of suitable substituents are halogen atoms such as fluorine and chlorine, amino groups such as —$NH_2$, alkylamino groups, dialkylamino groups, and cyano groups. The most preferred monodentate ligands is a phosphorus atom linked to three alkyl groups, together containing not more than 24 carbon atoms. More preferably, the alkyl groups do not contain more than 15 carbon atoms. Tri-n-butylphosphine is the most preferred monodentate ligand.

Preferably, at least one of $R_1$, $R_2$ and $R_3$ represents a substituted hydrocarbyl group containing a substituent capable of forming a complex with rhodium, in which case the ligand is a bidentate or tridentate ligand. For example, if one of $R_1$, $R_2$ and $R_3$ represents a group $R_4MR_5R_6$, in which $R_4$ is a bivalent organic group and $R_5$ and $R_6$ independently represent non-substituted hydrocarbyl groups, the ligand is a bidentate ligand in which two M atoms form a complexing linkage with rhodium.

Preferred bidentate ligands are ligands of the formula $R_1R_2MR_4MR_5R_6$. M and $R_4$ have the same meanings provided above and $R_1$, $R_2$, $R_5$ and $R_6$ independently represent an alkyl group having 1 to 4 carbon atoms. Even more preferred is the case in which $R_1$, $R_2$, $R_5$ and $R_6$ are methyl groups or where $R_1$ together with $R_2$ and/or $R_5$ together with $R_6$ represents a bivalent cyclic group having from 6 to 8 carbon atoms. Examples of suitable bivalent cyclic groups, formed by $R_1$ and $R_2$ or by $R_5$ and $R_6$ are 1,2 cyclohexylene and 1,2-cyclooctylene groups. $R_4$ preferably contains 2 to 5 carbon atoms. Most preferably $R_4$ is a $C_{2-5}$ alkylene group. Trimethylene is the most preferred $R_4$ group. Specific examples of suitable bidentate ligands are 1,2-bis(diethylphosphino) ethane; 1,2-bis(diisopropylphosphino) ethane; 1,3-bis(dimethylphosphino) propane; 1,3-bis(diethylphosphino) propane; 1,3-bis(diisopropylphosphino) propane; and 1,3-bis(cyclooctylenephosphino) propane.

The amount of bidentate ligand used in the catalyst system of the invention is usually in the range of 0.5 to 3 mol per gram atom of rhodium. More preferably the range is from 1 to 2 mol per gram atom of rhodium. The amount of monodentate ligands is usually in the range of 1–500, preferably in the range of 2–100, mol per gram atom of rhodium. Preferably at least stoichiometric amounts of ligand are used, particularly these are between 1 and 8 mol per gram atom of rhodium.

The catalyst system employs a rhodium cation source. This source may be a rhodium salt, a rhodium compound, or a rhodium complex. Examples of suitable rhodium compounds and complexes are rhodium nitrate and rhodium carbonyl complexes such as dirhodium octacarbonyl, tetrarhodium dodecacarbonyl, and hexarhodium hexadecacarbonyl.

Preferably, organic rhodium compounds are used such as rhodium carboxylates and organic rhodium carbonyl compounds. Examples of suitable organic rhodium compounds are rhodium acetate, rhodium di(carbonyl) acetylacetonate, 1,5-cyclooctadiene-rhodium (I) acetate and 1,5-cyclooctadiene-rhodium (I) acetylacetonate. acetylacetonate.

The amount of rhodium present in the catalyst system may vary but is generally between about 0.0001 and 0.5 gram atom rhodium per mol of unsaturated reactant compound. When ligands of the formula $MR_1R_2R_3$ are used, rhodium quantities between about 0.001 and 0.1 gram atom rhodium per mol of unsaturated reactant compound are most preferred.

The α-substituted, α-β-unsaturated carbonyl compounds, used as starting material in the process according to the invention may be represented by the formula

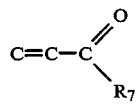

in which $R_7$ is a substituted or unsubstituted hydrocarbyl group and the free valences are linked to hydrogen atoms or other moieties. Preferably, reactant carbonyl compounds have the formula

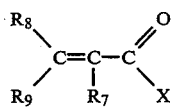

in which $R_7$ is an alkyl or substituted alkyl group, $R_8$ and $R_9$ independently represent a hydrogen atom or a substituted or nonsubstituted alkyl group and X is hydrogen, alkyl, alkoxy, hydroxy, amino or (di) alkylamino. Alkyl, alkoxy and (di)alkylamino groups represented by $R_7$, $R_8$, $R_9$ and X preferably contain from 1 to 4 carbon atoms. $R_7$ preferably represents a methyl group. At least one of $R_8$ and $R_9$ is preferably a hydrogen atom and X is preferably an alkoxy group. The methoxy group is the most preferred X configuration.

Examples of suitable carbonyl compounds include methylmethacrylate, ethylmethacrylate, methyltiglate, methacrylic acid and methacrylamide. Methylmethacrylate is a particularly preferred starting material because of the high selectivity of its conversion to methyl-α-formylisobutyrate which has particular commercial utility in pharmaceutical synthesis and as a chemical intermediary in the synthesis of numerous other chemicals such as food additives.

The carbon monoxide and hydrogen hydroformylation reactants are conveniently supplied to the reactor as such or they may be diluted with inert gases such as nitrogen. The molar ratio between carbon monoxide and hydrogen is generally between 2:1 and 1:2, but substantially equimolar amounts are preferred.

It is often practical and advantageous to perform the hydroformylation reaction in the presence of an additional solvent. Best results are usually obtained with polar, aprotic solvents. Examples include: ketones such as acetone and methyl ethyl ketone; ethers such as dimethyl ether, diethyl ether, dimethyl ether of diethylene glycol (diglyme), tetrahydrofuran, diisopropyl ether; and amides such as dimethylacetamide and N-methylpyrrolidone. N-methylpyrrolidone is a particularly preferred solvent.

The hydroformylation reaction according to the invention is carried out at moderate reaction conditions. Suitable reaction temperatures are generally between 10° C. and 200° C., preferably in the range from 50° to 150° C. The total reaction pressure is generally below 120 bar. Higher pressures are feasible, but not recommended, in view of the requirements the reaction equipment then has to fulfil. Preferably, pressures in the range of between 2 and 100 bar are used; most preferably they are in the range of between 5 and 80 bar.

The invention is illustrated by the following, nonlimiting examples. All experiments were performed in a 250 mL magnetically stirred "HASTELOY C" (trade mark) autoclave. All selectivities of α-hydroformylation products reported in the examples and accompanying tables are measured as a percentage of the total reaction products produced.

EXAMPLE 1

The autoclave was charged with 20 mL of methylmethacrylate, 0.1 mmol of rhodium di(carbonyl)acetylacetonate, 0.12 mmol of 1,3-bis(dimethylphosphino) propane (i) and 45 mL of solvent.

The autoclave was then flushed with an equimolar mixture of carbon monoxide and hydrogen and pressurized up to a total pressure of 60 bar (partial pressure of CO and H2 each 30 bar). The autoclave was then sealed and the mixture was heated to the reaction temperature (90° C.). After 2 hours the reaction mixture was cooled to room temperature and the pressure released.

The reaction rate and selectivity to methyl α-formylisobutyrate are shown in Table 1.

This example demonstrates the high alpha selectivity that is attainable without sacrifice to reaction rate when the process of the claimed invention is executed.

EXAMPLE 2

In a similar manner as described in Example 1, experiments were performed with catalyst systems containing the following ligands:

(ii) 1,3-bis(diethylphosphino) propane
(iii) 1,3-bis(diisopropylphosphino) propane
(iv) 1,3-bis(cyclooctylene phosphino) propane
(v) 1,3-bis(dimethylphosphino) propane
(vi) 1,2-bis(diethylphosphino) ethane The results of these experiments are shown in Table 1.

This example demonstrates the high selectivity of α-formylation products when the process of the instant invention is carried out and also demonstrated the consistency with which results are obtained.

EXAMPLE 3

In an analogous manner as described in Example 1 two experiments were carried out with catalyst systems containing 0.5 mmol of tributylphosphine and 0.5 mmol of triphenylphosphine, respectively. The reaction temperature was 80° C.

The results of these experiments are shown in Table 2.

This example demonstrates the improvement in alpha selectivity of hydroformylation reactions of the instant invention over those of the prior art.

TABLE 1

| Ligand | Rate (mol/gat · h) | Selectivity | Solvent |
| --- | --- | --- | --- |
| (i) | 890 | 97 | diglyme |
| (ii) | 890 | 91 | diglyme |
| (iii) | 1000 | 82 | diglyme |
| (iv) | 450 | 93 | diglyme |
| (v) | 220 | 98 | N-methyl pyrrolidone |
| (vi) | 500 | 91 | diglyme |

TABLE 2

| Ligand | Rate (mol/gat · h) | Selectivity | Solvent |
| --- | --- | --- | --- |
| Tributylphosphine | 1100 | 97 | diglyme |
| Triphenylphosphine-x | 600 | 89 | diglyme | x- for comparison only, not according to the invention.

While this invention has been described in detail for the purpose of illustration, it is not to be construed as limited thereby but is intended to cover all changes and modifications within the spirit and scope thereof.

What is claimed is:

1. A hydroformylation process comprising reacting α-substituted, α-β-unsaturated carbonyl compounds with carbon monoxide and hydrogen in the presence of a catalyst system comprising:
a) a source of rhodium cations; and
b) a source of ligands of the formula
$MR_1R_2R_3$ wherein M is a member the group consisting of phosphorus, arsenic and antimony; $R_1$, $R_2$ and $R_3$ are independently selected from the group consisting of hydrocarbyl groups and substituted hydrocarbyl groups, said hydrocarbyl and substituted hydrocarbyl groups together containing not more than 24 carbon atoms; wherein at least one of $R_1$, $R_2$ and $R_3$ is linked to M by an aliphatic carbon atom.

2. A process as claimed in claim 1, wherein said substituted hydrocarbyl group has the formula $R_4MR_5R_6$, wherein $R_4$ is a bivalent organic group, $R_5$ and $R_6$ are independently selected from the group consisting of hydrocarbyl groups and substituted hydrocarbyl groups, and M is selected from the group consisting of phosphorous, arsenic, and antimony.

3. The process of claim 1 wherein M is phosphorous.

4. The process of claim 1 wherein $R_1$, $R_2$, and $R_3$ are independently selected from the group consisting of substituted and unsubstituted alkyl groups.

5. A process as claimed in claim 4 wherein $R_1$, $R_2$, and $R_3$ independently comprise n-butyl groups.

6. The process of claim 1 wherein $R_1$, $R_2$, $R_5$ and $R_6$ are selected from the group consisting of $C_{1-4}$ alkyl groups, bivalent cyclic $C_{6-8}$ groups formed from the combination of $R_1$ together with $R_2$, and bivalent cyclic $C_{6-8}$ groups formed from the combination of $R_5$ together with $R_6$.

7. The process of claim 6 wherein the $C_{1-4}$ alkyl group is methyl.

8. The process of claim 6 wherein said bivalent cyclic $C_{6-8}$ groups are 1,2-cyclooctylene groups.

9. The process of claims 1 wherein $R_4$ is a trimethylene group.

10. The process of claim 1 wherein said source of rhodium cations is rhodium di(carbonyl) acetylacetonate.

11. The process of claim 1 wherein between 0.001 and 0.1 gram atoms of rhodium per mole of carbonyl compound are present.

12. The process of claim 1 wherein said carbonyl group is a compound of the formula

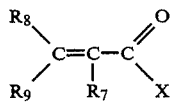

wherein $R_7$ is selected from the group consisting of substituted and unsubstituted alkyl groups; $R_8$ and $R_9$ are independently selected from the group consisting of hydrogen, unsubstituted, and substituted alkyl; and X is selected from the group consisting of hydrogen, alkyl, alkoxy, hydroxy, amino, and dialkylamino groups.

13. The process of claim 12 wherein said carbonyl compound is methylmethacrylate.

14. The process of claim 1 wherein carbon monoxide and hydrogen are present in substantially equimolar amounts.

15. The process of claim 1 conducted in the presence of a polar, aprotic solvent.

16. The process of claim 15 wherein said solvent is N-methylpyrrolidone.

17. The process of claim 1 wherein the reaction is carried out at a temperature between about 50° and 150° C.

18. The process of claim 1 wherein the reaction is carried out at a pressure between about 5 and 80 bar.

19. A hydroformylation process to selectively obtain α-formyl reaction products comprising reacting a carbonyl compound with carbon monoxide and hydrogen in the presence of a catalyst system comprising:
a) a source of rhodium cations selected from the group consisting of rhodium acetate, rhodium di(carbonyl) acetylacetonate, 1,5-cyclooctadiene, rhodium (I) acetate, and 1,5-cyclooctadiene-rhodium (I) acetylacetone; and
b) a source of ligands of the formula $MR_1R_2R_3$, wherein M is phosphorus;
$R_1$ and $R_2$ are $C_{1-4}$ alkyl groups,
$R_3$ is selected from the group consisting of $C_{1-4}$ alkyl and hydrocarbyl groups of the formula $R_4MR_5R_6$ wherein;
$R_4$ is a $C_{2-5}$ bivalent organic group,
$R_5$ and $R_6$ independently comprise hydrocarbyl groups which combine to form a bivalent cyclic $C_{6-8}$ group; and
at least one of R1, R2 and R3 is linked to M by an aliphatic carbon atom.

20. A hydroformylation process comprising reacting methylmethacrylate with carbon monoxide and hydrogen in the presence of a catalyst system comprising:
a) between 0.001 and 0.1 gram atoms of rhodium per mole of methylmethacrylate; and
b) between 1 and 2 mol per gram of rhodium of a ligand selected from the group consisting of 1,3-bis(dimethylphosphino) propane; 1,3-bis(diethylphosphino) propane; 1,2-bis(diethylphosphino) propane; 1,3-bis(cyclooctylene phosphino) propane; and tributylphosphine; said carbon monoxide and hydrogen being present in substantially equimolar quantities; said reaction being conducted between 50° and 150° C. at a pressure between 5 and 80 bar; said reaction producing α-formyl products at a selectivity greater than 90% based on total quantity of reaction products formed.

* * * * *